(12) United States Patent
Berkcan et al.

(10) Patent No.: US 9,364,362 B2
(45) Date of Patent: Jun. 14, 2016

(54) IMPLANTABLE DEVICE SYSTEM

(75) Inventors: Ertugrul Berkcan, Clifton Park, NY (US); Emad Andarawis Andarawis, Ballston Lake, NY (US)

(73) Assignee: General Electric Company, Niskayuna, NY (US)

( * ) Notice: Subject to any disclaimer, the term of this patent is extended or adjusted under 35 U.S.C. 154(b) by 1075 days.

(21) Appl. No.: 12/254,850

(22) Filed: Oct. 21, 2008

(65) Prior Publication Data

US 2010/0100079 A1    Apr. 22, 2010

(51) Int. Cl.
*A61B 5/00* (2006.01)
*A61F 5/00* (2006.01)
*A61B 17/135* (2006.01)

(52) U.S. Cl.
CPC ........... *A61F 5/0059* (2013.01); *A61B 17/1355* (2013.01); *A61F 5/003* (2013.01); *A61F 5/0003* (2013.01); *A61F 5/005* (2013.01); *A61F 5/0053* (2013.01); *A61F 5/0046* (2013.01); *A61F 2005/002* (2013.01)

(58) Field of Classification Search
CPC ... A61F 5/0003; A61F 5/0076; A61F 5/0013; A61F 5/0016; A61F 5/002; A61F 5/0023; A61F 5/005; A61F 5/0079; A61F 5/0083
USPC ......... 600/300, 372, 373, 544, 545, 546, 547, 600/549, 551, 558, 559, 561
See application file for complete search history.

(56) References Cited

U.S. PATENT DOCUMENTS

| | | | |
|---|---|---|---|
| 7,044,911 B2* | 5/2006 | Drinan et al. | 600/300 |
| 7,658,727 B1* | 2/2010 | Fernandes et al. | 604/265 |
| 7,933,562 B2* | 4/2011 | Rofougaran et al. | 455/80 |
| 2003/0092995 A1* | 5/2003 | Thompson | 600/473 |
| 2007/0106172 A1* | 5/2007 | Abreu | 600/549 |
| 2007/0255341 A1* | 11/2007 | Giftakis et al. | 607/46 |
| 2008/0172072 A1* | 7/2008 | Pool et al. | 606/151 |

* cited by examiner

*Primary Examiner* — Erik B Crawford
(74) *Attorney, Agent, or Firm* — John P. Darling

(57) ABSTRACT

An implantable device system is disclosed. The implantable device system includes, a first energy transceiver system, a second energy transceiver system at least partially implanted within an organic tissue and capable of communication with the first energy transceiver system, and a sensing system capable of communication with the second energy transceiver system. An implantable device system array is also disclosed. A method of monitoring a physical parameter is also disclosed.

11 Claims, 5 Drawing Sheets

IMPLANTABLE DEVICE SYSTEM

BACKGROUND

The invention relates generally to implantable devices, and more specifically to remotely interrogated implantable devices.

Certain medical conditions of the human body are controlled and/or corrected via a mechanical device implanted in the body, as opposed to a chemical "drug" route. Medical treatment of such conditions using a mechanical device can avoid possible side effects due to the ingestion of drugs.

Such devices are generally implanted within the human body close to the area where the therapeutic/corrective action is required. The overall management (monitoring and manipulation) of the state of operation of such traditionally available devices has required complicated procedures. Faulty execution of the complicated procedures can expose the patient to an infection or other medical issues. In addition, on-going post implantation management of such traditional devices usually requires direct and regular supervision by a qualified medical doctor, which limits the set of people who can derive benefit from such systems in a sustainable and cost-effective manner.

In addition, currently available implantable systems support a limited number of operation states, which limits the number of bodily conditions that can be addressed accurately. Further, most currently available implantable systems are based on invasive methods of interrogating the device such as puncturing the living tissue using a needle.

An implantable device that addresses one or more of the above drawbacks of traditionally available implantable systems would therefore be highly desirable.

BRIEF DESCRIPTION

Embodiments of the invention are directed towards an implantable device system and a method of operating the implantable device system.

An implantable device system in accordance with an embodiment of the invention includes a first energy transceiver system, a second energy transceiver system at least partially implanted within an organic tissue and capable of communication with the first energy transceiver system, and a sensing system capable of communication with the second energy transceiver system.

An implantable device system array in accordance with an embodiment of the invention includes a plurality of transceiver systems. Each of the transceiver systems includes, a first energy transceiver system, a second energy transceiver system at least partially implanted within an organic tissue and capable of communication with the first energy transceiver system, and a sensing system capable of communication with the second energy transceiver system and capable of performing a measurement operation of a physical parameter. Each of the plurality of transceiver systems is capable of independently communicating with any or all other transceiver systems of the plurality of transceiver systems.

A method of monitoring a physical parameter in accordance with an embodiment of the invention includes (a) transmitting energy from a first transceiver system to a second transceiver system, (b) using the energy within the second transceiver system to perform a physical parameter measurement operation, (c) transmitting a result of the physical parameter measurement operation from the second transceiver system to the first transceiver system, and (d) optionally independently repeating steps (a), (b), or (c). The second transceiver system is at least partially implanted within an organic tissue and is capable of communication with the first transceiver system.

These and other advantages and features will be more readily understood from the following detailed description of preferred embodiments of the invention that is provided in connection with the accompanying drawings.

DRAWINGS

DETAILED DESCRIPTION

Figure 1:
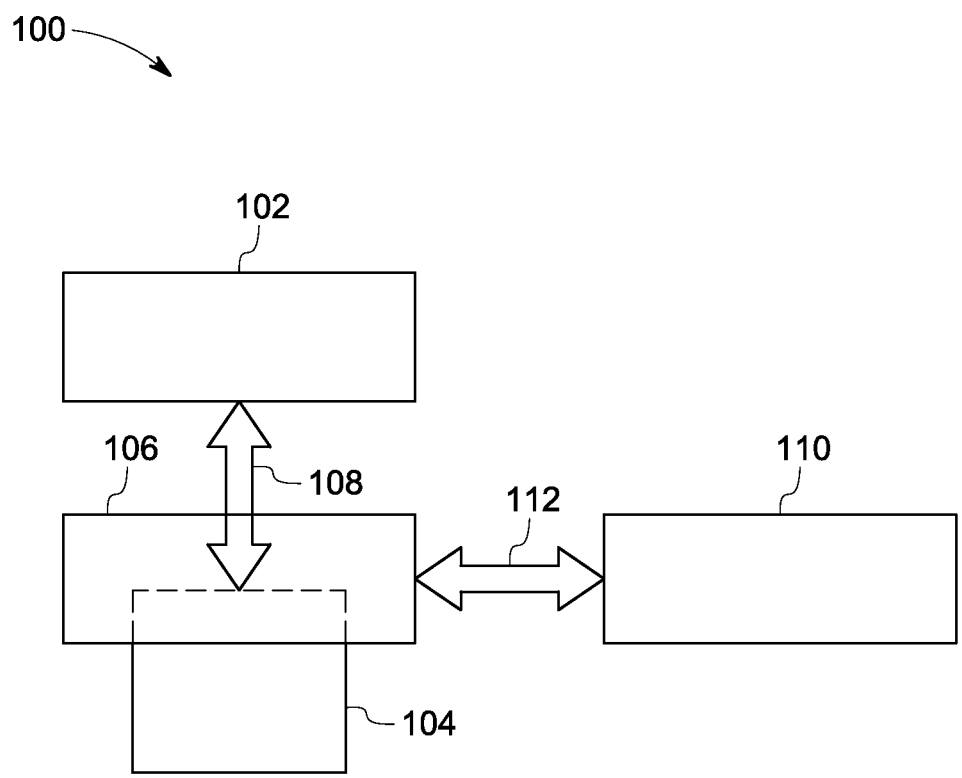
FIG. 1 is a schematic representation of an implantable device system in accordance with an exemplary embodiment of the invention.

In the following description, whenever a particular aspect or feature of an embodiment of the invention is said to comprise or include of at least one element of a group and combinations thereof, it is understood that the aspect or feature may comprise or include of any of the elements of the group, either individually or in combination with any of the other elements of that group.

As used herein, the term "adjacent," when used in context of discussion of different parts comprising the implantable device system may refer to the situation where the parts under discussion are immediately next to each other, or it may also refer to a situation wherein intervening parts are present between the parts under discussion.

As used herein, the term "communication," when used in context of discussion of at least two parts of the implantable device system means that any change in an electrical, magnetic, electromagnetic, mechanical, optical, acoustic, or other physical characteristic of one part is conveyed to, and therefore, detectable and measurable via, the other part. In one embodiment any or all of said physical characteristics may be conveyed via active communication, or they may be conveyed via passive communication such as reflection that is a function of the physical characteristic.

As used herein, the term "energy transceiver" refers to any device that has both a transmitter and a receiver. The circuitry and/or housing of the transmitter and receiver can be shared or can be independent. The transceiver device can include one or more transponder, and/or one or more transceiver, and/or one or more transverter. Said energy transceiver can include an electromagnetic radiation transceiver, an acoustic energy transceiver, and radiation transceiver, a vibration energy transceiver, a mechanical energy transceiver, and combinations thereof.

A used herein, the term "organic tissue" refers to any biological tissue. As used herein, the term "patient" refers to any living entity, for example, animals and human beings.

Typically, the term "organic tissue" will be used to refer to any biological tissue from which the "patient" is composed.

As used herein, the term "biocompatible material" refers to any natural or man-made material that comprises a whole or a part of an organic tissue, or of a biomedical device, such as an implantable device system, wherein the device system performs and/or augments and/or replaces a natural function of the organic tissue and/or is not rejected by the body's immune system and/or is not harmful to the body or tissue.

As used herein, the term "active component," when used in the context of discussion of one or more parts of the implantable device system means that the part requires a source of energy in order to be able to perform its function. As used herein, the term "passive component," when used in the context of discussion of one or more parts of the implantable device system means that the part does not require a source of energy in order to be able to perform its function.

Embodiments of the invention are directed towards an implantable device system capable of performing at least the following tasks: (1) sensing relevant physical parameters of its environment, (2) performing two-way communication with a second system at a remote location, (3) processing the sensed physical parameters, and/or any information obtained from the second system to determine whether a change in its own state of operation is desirable, (4) actively change its state of operation.

In accordance with an embodiment of the invention, an implantable device system 100 is shown schematically in FIG. 1. The implantable device system 100 includes a first energy transceiver system 102, a second energy transceiver system 104 at least partially implanted within an organic tissue 106 and capable of communication 108 with the first energy transceiver system, and a sensing system 110 capable of communication 112 with the second energy transceiver system 104 through the organic tissue 106. The first energy transceiver system 102, and/or the second electromagnetic transceiver system 104, and/or the sensing system 110, may be active components, or they may be passive components.

In one embodiment of the invention, the first energy transceiver system 102 and the second energy transceiver system 104 have the ability for two-way energy exchange, over a distance, between each other. The energy may be electromagnetic energy and may be used for the purpose of communication, or it may contain, possibly in encoded form, a value of a measured physical parameter. In certain embodiments, the exchanged energy may be stored within the first and/or of the second energy transceiver systems 102 and 104. Further, the exchanged energy may be used for energizing one or more components of the first and/or of the second energy transceiver systems 102 and 104. In one embodiment, the distance between the first energy transceiver system 102 and the second energy transceiver 104 system is about 15 centimeter (cm). In one embodiment, the distance between the first energy transceiver system 102 and the second energy transceiver system 104 is about 1 cm, when for example, the implantable device system is implanted close to the skin surface. In yet another embodiment, the distance between the first energy transceiver system 102 and the second energy transceiver system 104 is about 15 cm, when for example at least a part of the implantable device system is implanted or attached to an internal organ.

The energy exchange between the first energy transceiver system 102 and the second energy transceiver system 104 may be electromagnetic energy belonging to any region of the electromagnetic energy frequency spectrum. Non-limiting examples of the regions include microwave, radiowave, visible, infra-red, X-ray, gamma, and combinations thereof. Further, the energy exchange between the first energy transceiver system 102 and the second energy transceiver system 104 may be via acoustic, or vibrational energy. When the energy exchange is acoustic or virbrational the energy can belong to the ultrasonic or lower frequency ranges. In addition, when the energy is being used for communication, it may be transmitted as an analog signal. Further, the electromagnetic energy may be frequency modulated, amplitude modulated or phase modulated and may further include a carrier electromagnetic energy wave. Further, the energy may be encoded digitally. In one embodiment of the invention, the energy transfer between the first energy transceiver system 102 and the second energy transceiver system may be by mechanical energy. Non-limiting examples of the types of mechanical energy include sound energy and ultrasound energy and vibrational energy. Energy transfer schemes that employ a combination of electromagnetic and mechanical energies also fall within the purview of embodiments of the invention.

Figure 2:
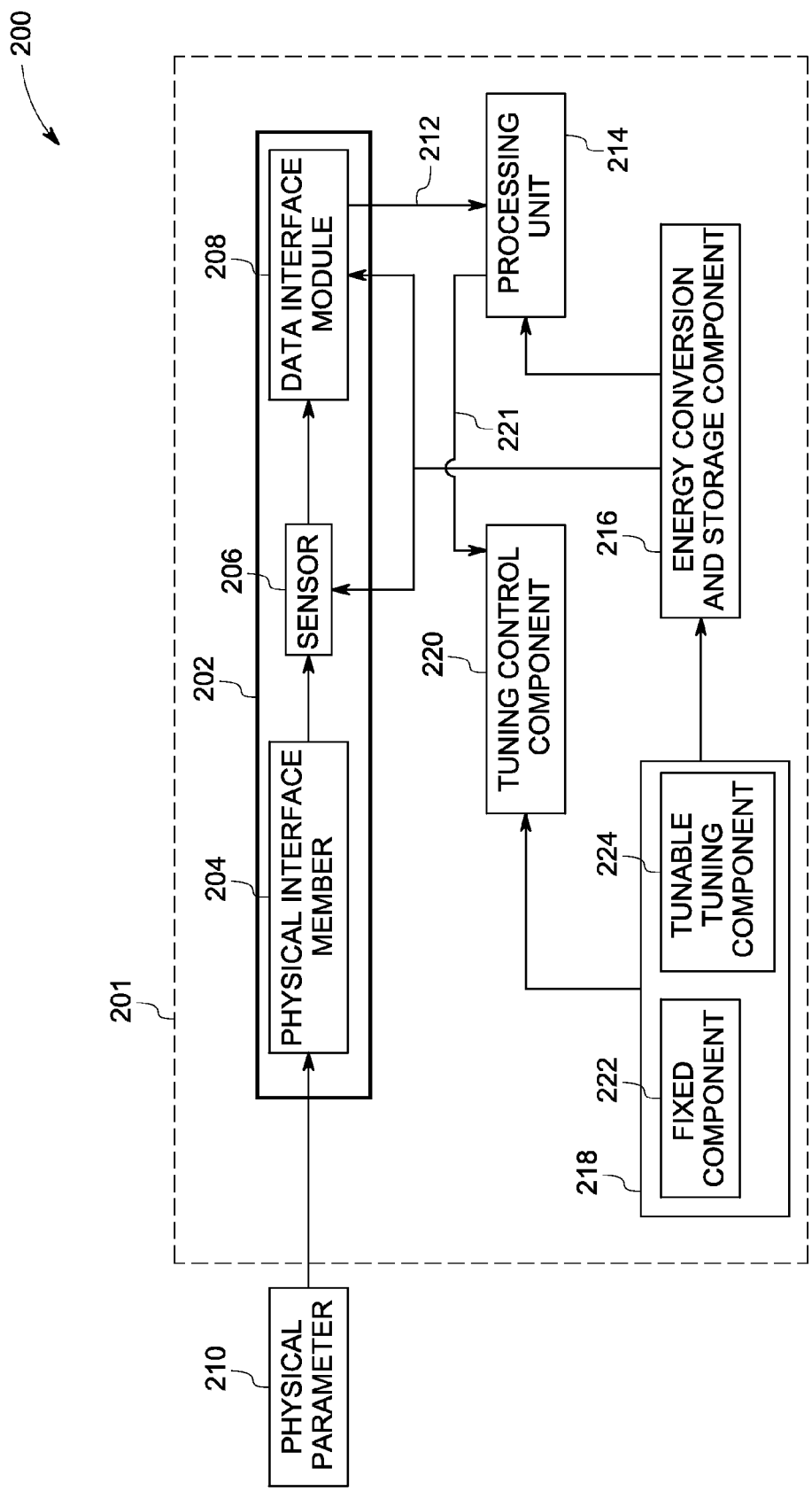
FIG. 2 is a block-diagram representation of a second energy transceiver system for use in the implantable device system of FIG. 1.

The implantable device system 100 can be fabricated in a variety of embodiments, depending upon its intended functionality. For instance, in one embodiment of the invention shown in FIG. 2, a second energy transceiver system 200 is housed at least partially within a biocompatible packaging 201 and includes a physical parameter sensing system 202. In the illustrated embodiment, the physical parameter sensing system 202 includes a physical interface member 204, a sensor 206, and a data interface module 208. The physical parameter sensing system 202 has the ability to perform, via the physical interface member 204 and the sensor 206, a sensing function of one or more physical parameters 210, and to communicate the result, via the data interface module 208 and a communication channel 212, to a processing unit 214. Non-limiting examples of physical parameters 210, which may be measured via the physical parameter sensing system 202, include physiological variables such as pressure, temperature, pH, electromagnetic energy, given chemical species, or mechanical parameters such as displacement, deformation, strain, or combinations thereof. The components of the physical parameter sensing system 202 each may be active or passive components.

The physical interface member 204 can be any suitable member that provides an interface to the environment. The one or more physical parameters 210 characterize what needs to be sensed, and the sensor 206 performs the operation of sensing the one or more physical parameters 210. In one embodiment of the invention, the physical interface member 204 may include a membrane, a pressure transfer element such as a diaphragm, a pressure conversion element, a temperature transferring element such as a heat pipe, a permeable membrane, one or more ion-selective electrodes, an electromagnetic antenna, or combinations thereof. Such a membrane may permit a selective transport of materials across itself. Further such membranes may contain auxiliary parts that provide, for instance, mechanical support. Suitable examples of materials from which such a physical interface member may be composed, include, but are not limited to, silicon, titanium glass, metal, ceramic, polymer, semiconductor, biocompatible materials, or other materials housed in biocompatible materials.

Non-limiting examples of possible types of sensors 206 include capacitive sensors, piezoelectric sensors, thermal sensors, inductive sensors, resistive sensors, mechanical, or combinations thereof. Further, the sensors may be biased and measured by way of a direct current (DC) technique, or an alternating current (AC) technique, or a combination of DC and AC techniques. It is possible that the bias level to the sensor 206 may be one of the factors determining the sensing characteristics such as selectivity and/or sensitivity towards one or another physical parameter 210. The AC and/or DC bias used in the operation of the sensor 206 may be an electrical current, an electrical voltage, or a combination thereof. Further, the AC or DC response of the sensor 206 during operation of the sensor 206 may be an electrical current, an electrical voltage, or a combination thereof. Typically, the sensor 206 makes available a result of the sensing function performed by it, as an analog reading. It is pointed out that the sensor 206 may be employed to perform quantitative or qualitative sensing function of the given one or more physical parameters 210.

In one embodiment of the invention, the sensor 206 includes a micro-electro-mechanical system (MEMS) sensor selected from the group consisting of MEMS based pressure sensors, MEMS incorporating circuit elements, and combinations thereof. It is likely a sensor 206, when constructed as a MEMS sensor, may offer additional advantages such, as reduced size, reduced energy consumption, reduced cost, high level of integration, amongst other advantages.

In one embodiment of the invention, the data interface module 208 is tasked with converting the analog reading, obtained as a result of the sensing function performed by the sensor 206, to an equivalent processed reading that is in a format that is acceptable to a processing unit 214. The processed reading may be in a digital format and communicated to the processing unit 214 through the communication channel 212. In one embodiment of the invention, the data interface module 208 includes at least one signal conditioning unit, at least one filtering unit, at least one amplifier, at least one comparator, at least one analog to digital converter, or combinations thereof.

In one embodiment of the invention, the second energy transceiver system 200 may itself be composed of a set of individual components. The set of individual components includes, a processing unit 214, an energy conversion and storage component 216, a tunable antenna 218, and a tuning control component 220. In one embodiment of the invention, the tunable antenna 218 further includes a fixed component 222, and a tunable tuning component 224.

The processing unit 214 may be any device that has the capability to accept, when provided in a suitable form, a result of a sensing operation performed by the physical parameter sensing system 202 and communicated to itself via the communication channel 212. The processing unit 214 may have the further ability to accept instructions from, for instance the patient and/or a medical doctor. The processing unit 214 has the further capability to process, via a variety of algorithms, the inputs that it receives to generate information. The information may, for example, be data sets characterizing the environment, or it may be instructions to be communicated to other components to modify their state of operation. The processing unit 214 has the further capability to communicate any of the information to a tuning control component 220 via a communication channel 221. The processing unit 214 also has the capability to communicate, directly or indirectly, with any or all of the other components comprising the implantable device system 100. The processing unit 214 is an active component and obtains the energy needed to perform its functions from an energy conversion and storage component 216. The processing unit 214 may include one or more components that allow for a control of the relationships between the signal that it receives as input and the signal that it generates as output. The choice of the type of processing unit 214 may be based on the specific requirements of the particular function that the implantable device system 100 is tasked to perform. For example, the processing unit can include, a microcontroller, a field programmable gate array (FPGA), a microprocessor, a programmable logic device, an application specific integrated circuit (ASIC), a digital signal processor, or combinations thereof.

The energy conversion and storage component 216 provides energy to all the active components within the implantable device system 100. The energy conversion and storage component 216 has the capability to receive, and/or convert, and/or store energy in a variety of forms. For instance, the energy conversion and storage component 216 may receive energy in the form of electromagnetic energy, and it may convert the same into chemical energy by charging a rechargeable battery. In the instant example, the charging of the rechargeable battery is equivalent to storing the electromagnetic energy within the rechargeable battery. This stored energy may be made available, as and when required, to the active components. It is pointed out that another "energy conversion" step may be required to convert the stored energy into a form that is acceptable to the given active component. It is further pointed out that the energy conversion and storage component 216 may be a monolithic component, or it may be a distributed component.

The operation of the energy conversion and storage component 216, depending on the specific requirements imposed by the particular function that the implantable device system 100 is tasked to perform, may be based on a variety of sources of energy. Non-limiting examples of the sources of energy for the energy conversion and storage component 216 are nuclear, chemical, thermophotovoltaic, piezoelectric, solar, and combinations thereof.

In embodiments of the implantable device system 100, wherein the source of energy of the energy conversion and storage component 216 is electromagnetic, the energy may be received in wireless mode. In one embodiment, other components of the implantable device system 100 also may have the ability to receive energy in wireless mode. It will be appreciated that the ability of the components of the implantable device system 100 to receive energy in wireless mode will likely result in a simplification and enhanced reliability of the implantable device system 100.

The energy conversion and storage component 216 may be placed wholly or partially within organic tissues composing the patient, or it may be placed outside of the patient. Non-limiting examples of organic tissue where the energy conversion and storage component 216 may be placed include a gastrointestinal tract, a thorax, and an abdomen. The energy conversion and storage component 216 may also be placed subcutaneously. For instance, when the source of energy of the energy conversion and storage component 216 is solar, the energy conversion and storage component 216 may be placed subcutaneously.

In one embodiment of the invention, the energy conversion and storage component 216 includes an energy storage capacitor, a rechargeable battery, primary cell battery, or combinations thereof. Suitable examples of energy storage capacitors include electrolytic capacitors and electric double layer capacitors (also known as ultracapacitors), supercapacitors, and mechanical energy storage systems such as a spring. In one embodiment, electric double layer capacitors are used due to their enhanced energy storage capacity and environmental friendliness, as compared to capacitors based on traditional technologies. The rechargeable battery can employ any known technology that is suitable. Non-limiting examples of possible technologies that may be used include, lead-acid, nickel-iron, nickel-cadmium, valve regulated lead acid, nickel-metal hydride, nickel-zinc, lithium ion, lithium polymer, lithium sulphur, nano titanate, lithium iron phosphate, thin film lithium, zinc-bromine, vanadium redox, sodium sulphur, molten salt, super iron, silver zinc, and alkaline. Further, the energy conversion and storage component 216 may include semiconductor components and circuitry such as p-n junctions and transistors. In one embodiment of the invention, energy may also be provided to the one or more active components from a power source that is not rechargeable. Any primary cell battery is suitable to serve as such a power source. Non-limiting examples of a primary cell battery include carbon-zinc cell, alkaline batteries, and combinations thereof.

In one embodiment, the energy conversion and storage component 216 comprises an AC-DC converter, a rectifier, a voltage regulator, or combinations thereof. The AC-DC converter can be based on any suitable known technology, such as, for example, semiconductor controlled rectification. A non-limiting example of a converter based on such a technology is the silicon controlled rectifier.

A tunable antenna 218 can be used to transmit the information in the form of electromagnetic energy to the first energy transceiver system 102. Further, the tunable antenna 218 is capable of being placed in a multitude of operational states through a tuning control component 220. The choice of the type of tunable antenna 218 is determined by a variety of factors, such as the type and amount of information that the tunable antenna 218 is tasked to transmit, or the specific characteristics of the first energy transceiver system 102, such as, for instance, its ability to receive information against a noisy background and choice of frequencies that it may use for communication.

In one embodiment of the invention, the tunable antenna 218 may include a fixed component 222 and/or a tunable tuning component 224. The tunable antenna 218 is tasked with communication with the first energy transceiver system 102. For instance, the tunable antenna 218 may receive information from the processing unit 214 via the tuning control component 220, and may transmit the same to the first energy transceiver system 102. Within the tunable antenna 218, the fixed component 222 serves the function of transmitting information to the first energy transceiver system 102, while the tunable tuning component 224 serves the function of placing the fixed component 222 into a particular operational state according to instructions the tunable tuning component 224 receives from the tuning control component 220. In other words, the tuning control component 220 serves to place, via the tunable tuning component 224, the tunable antenna 218 into any of the multitude of operational states that the tunable antenna 218 is capable of assuming.

In one embodiment of the invention, the fixed component 222 includes a radiator. Radiators are well known in the art. Non-limiting examples of a radiator include a broadband radiator, an inductive coil, a frequency dependent electromagnetic absorber, a quarter wave antenna, a dipole antenna, a half wave antenna, or combinations thereof.

In one embodiment of the invention, the tunable tuning component 224 comprises a tunable electromagnetic excitation source. Non-limiting examples of the tunable electromagnetic excitation source include a capacitor, an inductor, or combinations thereof.

The operational state of the tunable antenna 218 may be expressed via a number of operational parameters, including its impedance and its frequency range of operation, and a number of design parameter including its Q-factor. These parameters, in turn determine the transmission and reception characteristics of the tunable antenna 218 toward any given range of frequencies of electromagnetic radiation.

In one embodiment of the invention, the tunable tuning component 224 is capable of modifying an impedance state of the tunable antenna 218 by a fraction of a percent and by up to several hundreds of percent.

In one embodiment of the invention, the tunable tuning component 224 is capable of modifying a frequency of operation of the fixed component 222 by a fraction of a percent and by up to several hundreds of percent. The amount of modification possible of the frequency of operation of the fixed component 222 may depend upon, amongst other factors, the Q-factor of tunable antenna 218.

The choice of frequency of operation of the fixed component 222 is a function of several factors, such as for instance, the medium between the first energy transceiver system 102 and the second energy transceiver system 104. In one embodiment of the invention, the frequency of operation of the fixed component 222 lies within the range from about 100 kiloHertz to about 10 megaHertz. In one embodiment of the invention, the frequency of operation of the fixed component 222 lies within the range from about 100 kiloHertz to about 1 megaHertz.

The tuning control component 220 is under the control of the processing unit 214. The exact set of functions that the tuning control component 220 performs may be based on the specific requirements of the particular task that the implantable device system 100 is tasked to perform. For instance, the processing unit 214, based on predetermined algorithms, processes the results of the sensing operation performed by the physical parameter sensing system 202 to obtain data sets characterizing the environment. Based on a predetermined analysis protocol on the data sets, the processing unit 214 communicates instructions to the tuning control component 220. The tuning control component 220, under the influence of these instructions, places the tunable antenna 218 into one of the multitude of operational states of the tunable antenna 218.

Figure 3:
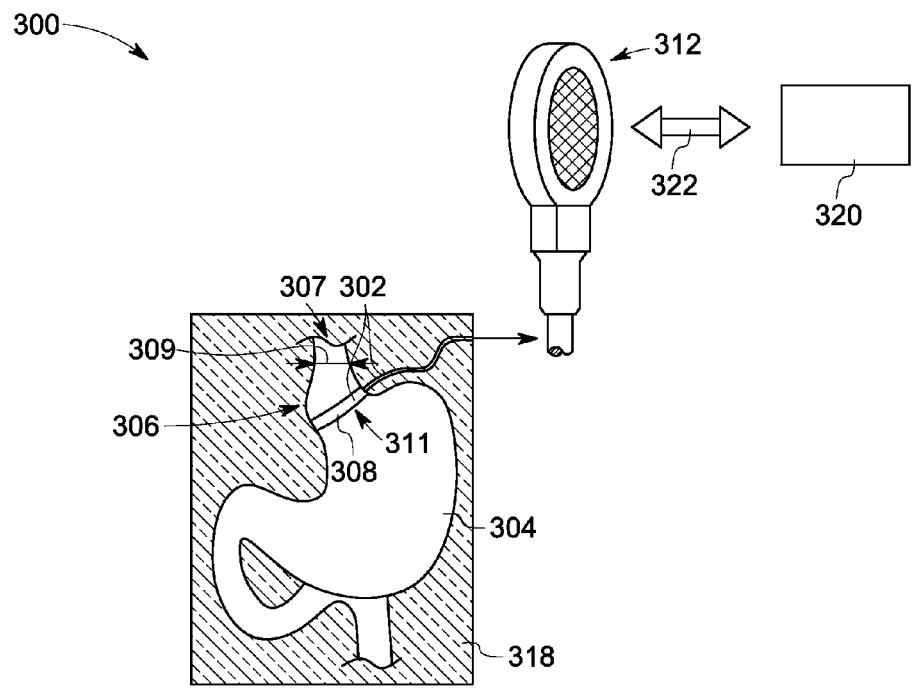
FIG. 3 is a schematic representation of an implantable device system in accordance with an exemplary embodiment of the invention.

In one embodiment 300 of the invention shown in FIG. 3, the implantable device system 100 serves as a gastrointestinal tract restriction device system 302 containing at least one gastrointestinal tract restricting structure, such as the deformation member 308. FIG. 3 shows a gastrointestinal tract restriction device system 302 attached to a human stomach 304 in the vicinity of an esophagogastric junction 306 which contains an esophagogastric orifice 307 that has a cross-sectional area 309. The gastrointestinal tract restriction device system 302 further includes a deformation member 308. One end of the deformation member 308 mates with a sealable port 312. The sealable port 312 can be attached to the human body such that it is at least partially subcutaneous. As discussed further below, the sealable port 312 may facilitate non-invasive control of the cross-sectional area 309 of the esophagogastric orifice 307. The general viscera 318 surrounding the gastrointestinal tract restriction device system 302 constitute an embodiment of the organic tissue 106.

The sealable port 312 can be any mechanical or electromechanical device that facilitates the introduction of fluids within the deformation member 308 when the deformation member 308 is in the form of a hollow tube. The sealable port 312, depending on its location within the implantable device system 302, may be composed of a biocompatible material. Non-limiting examples of materials from which the sealable port may be composed are, polymers, plastic materials, thermoplastic materials, and metals.

The introduced fluids can be any biocompatible liquid or gas. Non-limiting examples of fluids that may be introduced within the deformation member 308 when it is in the form of a hollow tube are, isotonic salt solution, saline solution, and combinations thereof.

The embodiment illustrated in FIG. 3 contains a first energy transceiver system 102 (not shown), and a second energy transceiver system 200 (not shown) containing a physical parameter sensing system 202 (not shown) and a processing unit 214 (not shown). The processing unit 214 may have the further ability to control the gastrointestinal tract restriction device system 302 in accordance with an activity schedule, and/or in accordance with sensing operations performed by the physical parameter sensing system 202, and/or in accordance with instructions received from the patient and/or a medical doctor. For instance, the processing unit 214 may instruct the physical parameter sensing system 202 to perform a sensing operation of the physiological variable "pressure." Non-limiting examples of the types of measurements associated with the physiological variable "pressure" include measurement of a pressure wave at any location along the gastrointestinal tract that may be produced, for instance, due to peristaltic contractions induced due to food boluses in the gastrointestinal tract, or a strain in the gastrointestinal tract restriction device system 302, or a stress in the gastrointestinal tract restriction device system 302.

In one embodiment of the invention, the processing unit 214 may instruct the physical parameter sensing system 202 to detect flow of food through the gastrointestinal tract. When such a flow of food is detected by the physical parameter sensing system 202, the processing unit 214 may instruct the gastrointestinal tract restriction device system 302 to induce a restriction in the gastrointestinal tract through a deformation of the deformation member 308. If such detection were to be performed continuously, then an appropriate deformation of the deformation member 308 can be induced only when food is being ingested. It will be appreciated that such a scheme will likely limit both the erosion of the tissue that is surrounded by the deformation member 308, and also may reduce energy consumption of the gastrointestinal tract restriction device system 302. It will be appreciated that the above feature would facilitate use of the gastrointestinal tract restriction device system 302 by a patients having, amongst other things, differing eating habits and needs.

The gastrointestinal tract restriction device system 302 can be used, for instance, to control the cross-sectional area 309 of the esophagogastric orifice 307. For instance, in one embodiment, the deformation member 308 partially or fully circumscribes the esophagogastric junction 306 to form a partial or complete "loop." The "interior" area 311, enclosed within the loop, may be changed by bringing about a suitable deformation of the deformation member 308. For instance, in one embodiment of the invention the deformation member 308 may be a hollow tube made of a pliant material that partially or fully circumscribes the esophagogastric junction 306 such that the loop that it forms has an initial area, and is in physical contact with, i.e., it embraces, the esophagogastric junction 306. It will be appreciated that any decrease in the interior area 311 of the loop will result in a decrease in the cross-sectional area 309 of the esophagogastric orifice 307. The size of the interior area 311 of the deformation member 308 (in this instant, of the hollow tube) may be decreased by pumping fluid (discussed below), via the sealable port 312, into the hollow tube. The pumping of the fluid into the hollow tube results in a build up of pressure within the hollow tube that can again be sensed ("monitored") via the physical parameter sensing system 202. The build up of pressure within the hollow tube results, because the hollow tube is made of pliant material, in a decrease in the interior area 311. On the other hand, a withdrawal of the fluid from the hollow tube 308, via the sealable port 312, will cause a decrease of pressure within the hollow tube, which will result in an increase in the interior area 311. In general the gastrointestinal tract restriction device system 302 can be attached at any other suitable location along the gastrointestinal tract of the patient.

In other embodiments of the invention the deformation member 308 may not be in the form of a hollow tube that utilizes introduction/removal and/or retention of fluid to change its shape and/or dimensions. It is conceivable that such a design may mitigate some of the risks, likely present in embodiments that contain a hollow tube and utilize fluids for their operation, associated with the possibility of leaking of the fluid through, for instance, the material composing the hollow tube.

The deformation member 308 can be composed of any material that is suitable for implantation within given organic tissue. Further, the deformation member 308 can be in any shape, and have any dimensions, that are appropriate for the given situation. For instance, as discussed herein, the deformation member 308 can be in the shape of a hollow tube. Also, any suitable mechanism, appropriate for the given material from which the deformable material 308 is composed, may be used to induce the deformation of the deformation member 308. For instance, if the deformation member 308 is composed of a shape memory alloy, Joule heating due to the passage of an electric current within the deformation member 308 may induce a deformation and/or change in tension, within the deformation member 308. The ability of the deformation member 308 to restrict the esophagogastric orifice 307 is therefore controllable via the thus induced deformation and/or the change in tension of the shape memory alloy from which it is composed.

It is likely that a restriction of the esophagogastric orifice 307 may result in a physiological feeling of satiation within in the patient. The gastrointestinal tract restriction device system 302 disclosed herein can be useful in the treatment of patients suffering from eating disorders such as compulsive overeating and bulimia nervosa. It may also be helpful in the treatment of, for instance, morbid obesity. On the other hand, it is conceivable that detection of multiple physiologic variables may be used to determine the amount of deformation ("corrective response") required of the deformation member 308. Embodiments of the invention may also incorporate multimodality therapy such as gastrointestinal tract restriction, in conjunction with other modalities such as neurostimulators, gastrointestinal tract muscle stimulators, gastrointestinal tract balloons, and bulking devices.

The deformation member 308 may be composed of any thermally, electrically, or mechanically deformable material. Non-limiting examples of metallic materials from which the deformation member 308 may be composed include, nickel-titanium alloys, stainless steel, titanium, cobalt, chromium. Non-limiting examples of semiconducting materials from which the deformation member 308 may be composed include silicon. Non-limiting examples of elastic materials from which the deformation member 308 may be composed include silicone, polyurethane, silicone elastomer, polypropylene, Alloderm™ (available from, LifeCell Corporation, Delaware, One Millennium Way, Branchburg, N.J. 08876), Surgisis™ (available from, Cook Biotech, Inc., Indiana 1425 Innovation Place, West Lafayette, Ind. 47906), polyesters, poly-tetrafluoroethene (PTFE), polyvinylidene fluoride (PVDF), and polyester.

In one embodiment, the invention may include a pumping apparatus including a pump 320 and fluid communication line 322, capable of pumping fluid into or out of the hollow tube. For example, the pumping apparatus 318 may include one or more valves (not shown) and/or one or more motors (not shown), such as hydraulic or a pneumatic motors. The pumping apparatus is disposed so that it is capable of pumping fluid into or out of the hollow tube via for instance, the sealable port 312. The pumping apparatus may be capable of pumping fluid, in a step manner, or in a continuous manner, or in a combination of a step and a continuous manner. The processing unit 214 may also be adapted to control pumping apparatus 318 according to, for instance, a patient activity schedule. The pumping apparatus 318 may further include a fluid reservoir (not shown) connected to the motor, and having for instance, a variable volume.

In one embodiment of the invention, the physical parameter sensing system 202 is capable to measuring a pressure of the deformation member 308 when it is in the form of a hollow tube, when the pressure is within the range of about 200 milli meters of mercury to about 1550 milli meters of mercury. In another embodiment, the physical parameter sensing system 202 is capable to measuring the pressure of the elastic member 302 when the pressure is within the range of about 100 milli meters of mercury to about 300 milli meters of mercury. In yet another embodiment, the physical parameter sensing system 202 is capable to measuring the pressure of the elastic member 302 when the pressure is within the range of about 150 milli meters of mercury to about 400 milli meters of mercury.

In one embodiment of the invention, the second energy transceiver system 200 of the implantable device system 100 is housed in a biocompatible packaging 201. Non-limiting examples of materials from which such biocompatible packaging may be composed include, titanium, samarium cobalt, calcium oxide, cobalt oxide, polystyrenes, polyphosphoester, polyphosphazenes, aliphatic polyesters, natural polymers, or combinations thereof. The choice of the particular biomaterial used for a specific application is guided by host of considerations, including but not limited to, toxicological, biocompatibility, pathobiological, immune-response, specific anatomical site of implant, mechanical and/or electrical performance requirements, and ethical.

In one embodiment of the invention, the implantable system 100 has the ability to assess its own "state of health" based on some internal test routines and/or additional sensing modalities. It will be appreciated that such ability facilitates, in case of a malfunction, the diagnosis of the malfunction.

Figure 4:
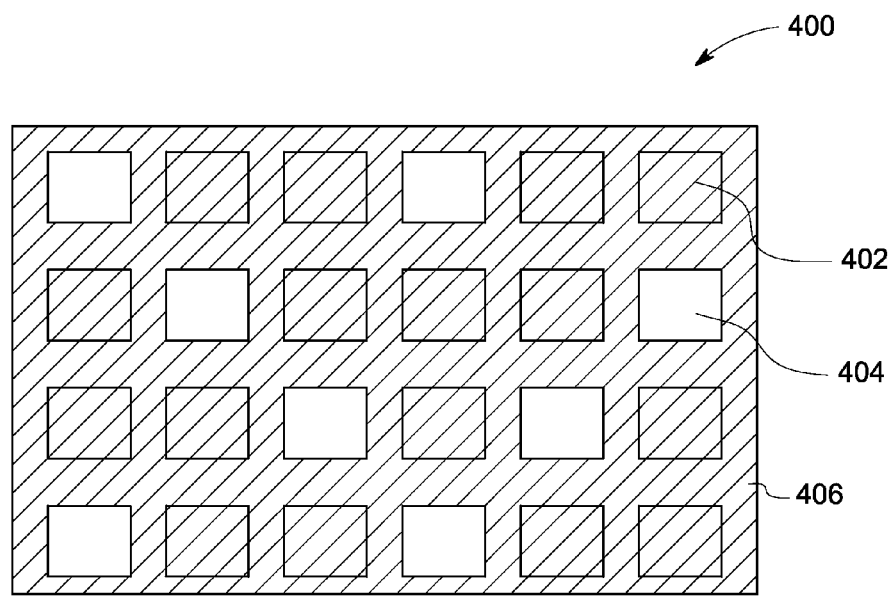
FIG. 4 is a schematic representation of an implantable device system array in accordance with an exemplary embodiment of the invention.

According to one embodiment of invention, an implantable device system array 400, as shown in FIG. 4, is disclosed. The implantable device system array 400 includes a plurality of transceiver systems, two examples of which are indicated via reference numerals 402 and 404, wherein each of the transceiver systems includes a first energy transceiver system (not shown), a second energy transceiver system (not shown) at least partially implanted within an organic tissue 406 and capable of communication with the first energy transceiver system, and a physical parameter sensing system (not shown) capable of communication with the second energy transceiver system and capable of performing a measurement operation of a physical parameter. In one embodiment of the invention, each of the plurality of transceiver systems is capable of independently communicating with any or all other transceiver systems of the plurality of transceiver systems comprising the array 400. In one embodiment of the invention, a medium between the plurality of transceiver systems that comprise the array 400 includes organic tissue 406. The plurality of transceiver systems comprising the array 400 may be fully or partially embedded within the organic tissue 406 as is indicated by the transceiver systems 402 and 404 respectively.

Figure 5:
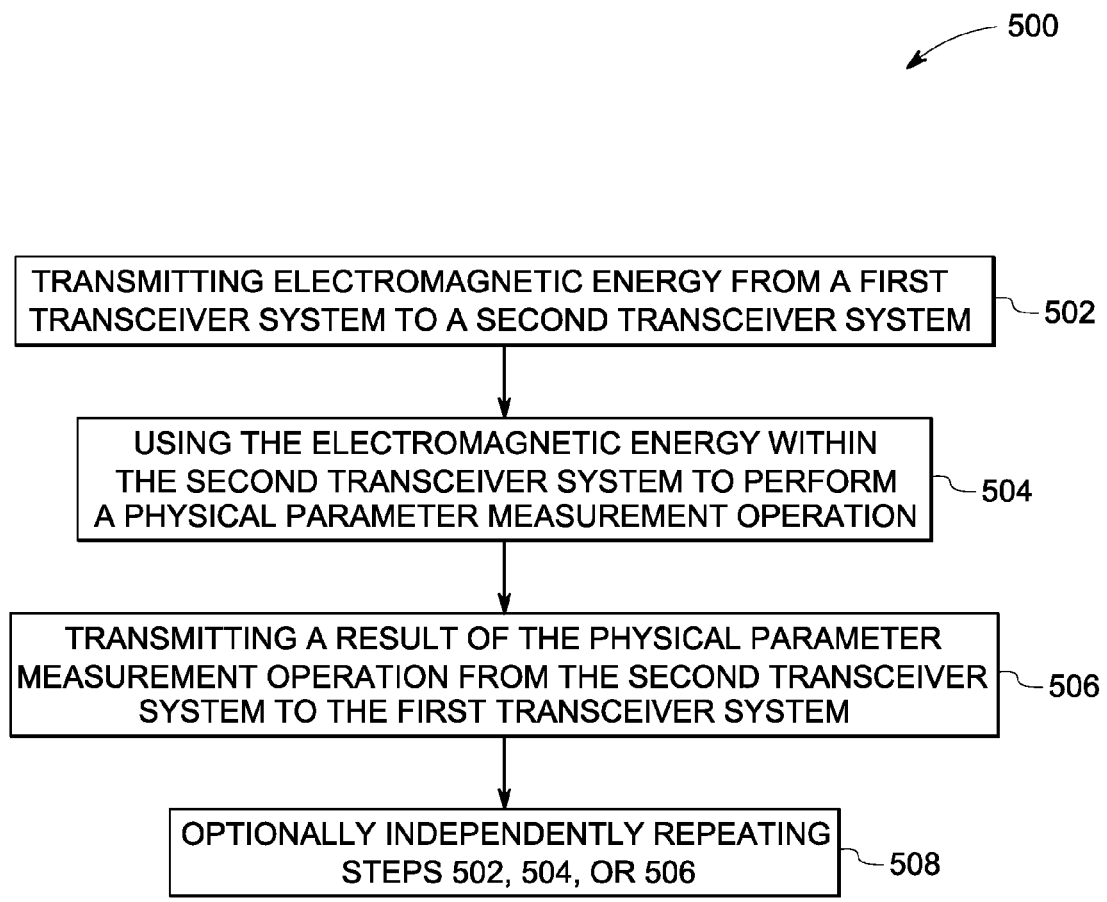
FIG. 5 illustrates a process flow of a physical parameter sensing operation in accordance with an exemplary embodiment of the invention.

A method 500 of monitoring a physical parameter is disclosed, as shown via the flow chart in FIG. 5. At step 502, the method 500 includes transmitting electromagnetic energy from a first transceiver system to a second transceiver system. In one embodiment of the invention, the first and the second transceiver systems are substantially of the same type as the first energy transceiver system 102, and the second energy transceiver system 104 respectively. Further, as described herein, the energy may be used for the purpose of communication, or it may be used for the purpose of energizing components of the implantable device system 100. This is followed by step 504, which includes using the energy within the second transceiver system to perform a physical parameter measurement operation. In one embodiment of the invention, the physical parameter measurement operation may be performed by a physical parameter sensing system that is substantially of the same type as the physical parameter sensing system 202. The next step 506 includes transmitting a result of the physical parameter measurement operation from the second transceiver system to the first transceiver system. The next step 508 includes optionally independently repeating steps 502, 504, or 506, wherein the second transceiver system is at least partially implanted within an organic tissue and is capable of communication with the first transceiver system.

In one embodiment of the invention, the electromagnetic energy transmitted at step 502 and/or step 506 lies within a frequency range between about 75 kiloHertz to about 15 megaHertz. In one embodiment of the invention, the electromagnetic energy transmitted at step 502 and/or step 506 lies within a frequency range between about 400 kiloHertz to about 650 kiloHertz. In one embodiment of the invention, the electromagnetic energy transmitted at step 502 and/or 506 lies within a frequency range between about 125 kiloHertz to about 650 kiloHertz.

Figure 6:
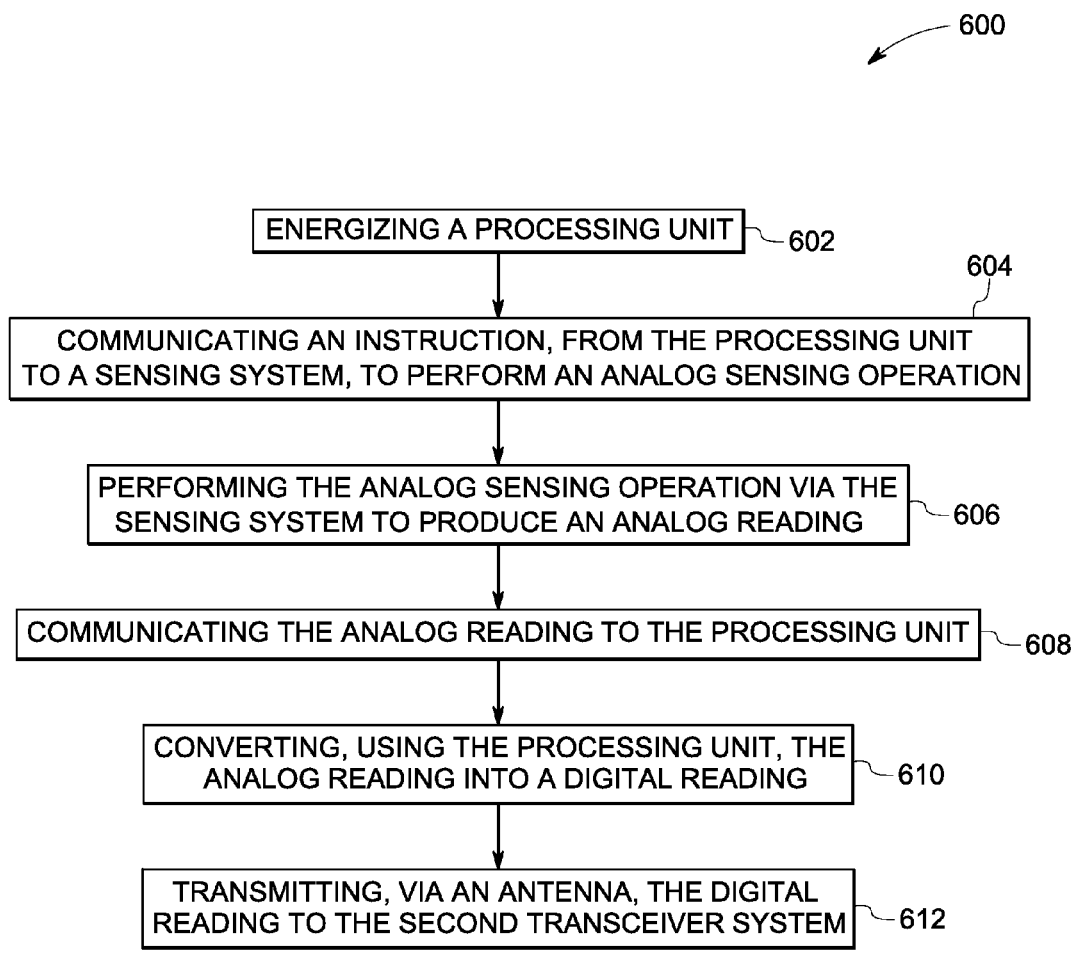
FIG. 6 illustrates a process flow of a communication operation in accordance with an exemplary embodiment of the invention.

According to one embodiment of the invention, a method 600 of performing a physical parameter measurement operation is disclosed, as shown via the flow chart of FIG. 6. The method 600 includes, at step 602, energizing a processing unit, such as the processing unit 214. This is followed by step 604 that includes communicating an instruction, from the processing unit to a sensing system, to perform an analog sensing operation. In one embodiment of the invention, the sensing system is substantially of the same type as the physical parameter sensing system 202. Next, step 606 includes performing the analog sensing operation via the sensing system to produce an analog reading. Next step 608 includes communicating the analog reading to the processing unit. Next, step 610 includes converting, using the processing unit, the analog reading into a digital reading. The next step 612 includes transmitting, via an antenna, the digital reading to the second transceiver system. In one embodiment of the invention, the antenna is substantially of the same type as the tunable antenna 218. In one embodiment of the invention, the second transceiver system is substantially of the same type as the second energy transceiver system 104.

In one embodiment of the invention, it is possible to fabricate the implantable device system 100 without the use of any high permeability materials. It is likely that this capability enables the implantable device system to operate substantially unhindered even in the presence of magnetic fields, such as those that are encountered during magnetic resonance imaging scanning. It is possible that enables the implantable device system 100 to operate within high magnetic fields of up to about 10 Tesla.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed as new and desired to be protected by Letters Patent of the United States is:

1. An implantable device system comprising:
    a first energy transceiver system; and
    a second energy transceiver system implanted within an organic tissue that passively communicates with the first energy transceiver system through the organic tissue, wherein the second energy transceiver system comprises a physical parameter sensing system, wherein the physical parameter sensing system comprises passive components,
        wherein the physical parameter sensing system performs a sensing function of one or more physical parameters and interfaces the sensed one or more parameters to the second energy transceiver system, wherein the physical parameter sensing system comprises a physical interface member, a sensor, and a data interface module, wherein the physical interface member is selected from the group consisting of a membrane, a diaphragm, a pressure conversion element, a heat pipe, a permeable membrane, one or more ion-selective electrodes, an electromagnetic antenna, and combinations thereof,
        wherein the second energy transceiver system modulates energy received from the first energy transceiver system to passively communicate the sensed one or more parameters and control an interior area within the organic tissue based on at least the sensing function performed by the physical parameter sensing system; and
        wherein the second energy transceiver system is housed in a biocompatible packaging selected from the group consisting of samarium cobalt, calcium oxide, cobalt oxide, and combinations thereof, wherein the implantable device system comprises a gastrointestinal tract restriction device system.

2. The implantable device system of claim 1, wherein the first energy transceiver system and the second energy transceiver system are separated by a distance of up to about 15 cm.

3. The implantable device system of claim 1, wherein the gastrointestinal tract restriction device further comprises a deformation member implanted within the organic tissue, wherein the deformation member further comprises a sealable port.

4. The implantable device system of claim 3, wherein the deformation member is a hollow tube.

5. The implantable device system of claim 4, wherein the hollow tube is in the form of a loop.

6. The implantable device system of claim 1, wherein the physical interface member is composed of a material selected from the group consisting of silicon, titanium glass, metal, ceramic, polymer, semiconductor, biocompatible materials, and combinations thereof.

7. The implantable device system of claim 1, wherein the sensor is selected from the group consisting of a distributed sensor comprising a capacitive sensor, a piezoelectric sensor, a thermal sensor, an inductive sensor, a resistive sensor, a mechanical sensor, and combinations thereof.

8. The implantable device system of claim 7, wherein the sensor includes at least one MEMS sensor selected from the group consisting of MEMS based pressure sensors, MEMS incorporating circuit elements, and combinations thereof.

9. The implantable device system of claim 1, wherein the sensor quantitatively detects a physical quantity selected from the group consisting of pressure, temperature, pH, electromagnetic energy, given chemical species, mechanical parameters, and combinations thereof.

10. The implantable device system of claim 1, wherein the data interface module is selected from the group consisting of at least one signal conditioning unit, at least one filtering unit, at least one amplifier, at least one comparator, at least one analog to digital converter, and combinations thereof.

11. The implantable device system of claim 1, wherein the first energy transceiver system is selected from the group consisting of an electromagnetic radiation transceiver, an acoustic energy transceiver, a mechanical energy transceiver, a vibration energy transceiver, and a radiation transceiver.

* * * * *